US012332156B2

(12) United States Patent
Zhang et al.

(10) Patent No.: US 12,332,156 B2
(45) Date of Patent: Jun. 17, 2025

(54) SOIL SAMPLE DIDESTION DEVICE

(71) Applicant: NORTHWEST INSTITUTE OF ECO-ENVIRONMENT AND RESOURCES, CAS, Lanzhou (CN)

(72) Inventors: Caixia Zhang, Lanzhou (CN); Yunfa Miao, Lanzhou (CN); Ningjing Tan, Lanzhou (CN); Yongtao Zhao, Lanzhou (CN); Xuelian Wang, Lanzhou (CN)

(73) Assignee: NORTHWEST INSTITUTE OF ECO-ENVIRONMENT AND RESOURCES, CAS, Lanzhou (CN)

( * ) Notice: Subject to any disclaimer, the term of this patent is extended or adjusted under 35 U.S.C. 154(b) by 0 days.

(21) Appl. No.: 19/034,240

(22) Filed: Jan. 22, 2025

(65) Prior Publication Data
US 2025/0164363 A1  May 22, 2025

(30) Foreign Application Priority Data
Apr. 19, 2024  (CN) .......................... 202410473203.6

(51) Int. Cl.
*G01N 1/40* (2006.01)
*G01N 33/24* (2006.01)

(52) U.S. Cl.
CPC ........... *G01N 1/4044* (2013.01); *G01N 33/24* (2013.01)

(58) Field of Classification Search
CPC .............................. G01N 1/4044; G01N 33/24
See application file for complete search history.

(56) References Cited

U.S. PATENT DOCUMENTS

2017/0320032 A1* 11/2017 Collins, Jr. ............... B01L 7/00

FOREIGN PATENT DOCUMENTS

| CN | 206656909 U | 11/2017 |
| CN | 111854365 A | 10/2020 |
| CN | 212674588 U | 3/2021 |
| CN | 216484253 U | 5/2022 |
| WO | WO-2021001716 A1 * | 1/2021 ............ C12M 21/04 |

OTHER PUBLICATIONS

Yan Zhou et al., "ICP-MS Determination of Trace Elements in Soil from Lead-Zinc Ore Mining Area", Physical Testing and Chemical Analysis(Part B:Chemical Analysis), Dec. 31, 2011, vol. 47, No. 5, pp. 583-585.

* cited by examiner

*Primary Examiner* — Jennifer Wecker (57) ABSTRACT

A soil sample digestion device, including a base, a driving mechanism, a first disk, a heating mechanism, a digestion vessel, a second disk and two liquid adding mechanisms. The driving mechanism and the first disk are mounted on the base. The heating mechanism and the digestion vessel are mounted on the first disk. The heating mechanism is configured to heat a solution in the digestion vessel. The second disk is mounted on the driving mechanism, and is configured to be driven by the driving mechanism to ascend and descend, or rotate relative to the first disk. The two liquid adding mechanisms are mounted on the second disk, and are configured for liquid addition to the digestion vessel.

7 Claims, 5 Drawing Sheets

SOIL SAMPLE DIDESTION DEVICE

CROSS-REFERENCE TO RELATED APPLICATIONS

This application claims the benefit of priority from Chinese Patent Application No. 202410473203.6, filed on Apr. 19, 2024. The content of the aforementioned application, including any intervening amendments made thereto, is incorporated herein by reference in its entirety.

TECHNICAL FIELD

This application relates to material testing or analysis, and more particularly to a soil sample digestion device.

BACKGROUND

The soil contains a variety of trace elements and rare earth elements. Some trace elements are essential for the growth and survival of plants and animals, which mainly include boron, molybdenum, manganese, zinc, copper, cobalt, nickel, chromium, vanadium, barium, strontium, gallium and 17 rare earth elements including lanthanum, samarium, europium, gadolinium, terbium, dysprosium, holmium, erbium, thulium, ytterbium, lutetium, scandium and yttrium. Trace elements in soil are affected by many factors such as significant differences in natural conditions and soil types. The supply level of trace elements in soil is jointly affected by soil parent material, soil type, soil physical and chemical properties, water dynamics, etc. In order to accurately determine the content of these elements, the soil particles must be digested to form an aqueous solution and then analyzed using an inductively coupled plasma mass spectrometer.

In the prior art, the method for detecting soil is commonly carried out as follows. The soil is sampled, sent to the laboratory and digested, such that the solid sample is processed into a liquid sample. Then, the liquid sample is analyzed. When performing digestion, it is necessary to add a corresponding liquid to the soil sample. Generally, the soil sample is manually added with a digestion solution, manually placed in a heating mechanism for heating, and subjected to subsequent analysis and operation. This leads to high labor intensity and low efficiency. Moreover, the liquids such as nitric acid and hydrofluoric acid used in this method are highly corrosive, which may easily pose a health threat to an operator.

SUMMARY

An object of the disclosure is to provide a soil sample digestion device that can achieve an improvement of automation level, a reduction in labor intensity, thereby saving time and effort, resulting in high efficiency.

In order to achieve the above object, the following technical solutions are adopted.

This application provides a soil sample digestion device, comprising:
 a base;
 a driving mechanism;
 a first disk;
 a heating mechanism;
 a digestion vessel;
 a second disk;
 a first liquid adding mechanism; and
 a second liquid adding mechanism;

wherein the driving mechanism and the first disk are mounted on the base; the heating mechanism and the digestion vessel are mounted on the first disk; the heating mechanism is configured to heat a solution in the digestion vessel; the second disk is mounted on the driving mechanism, and is configured to be driven by the driving mechanism to ascend and descend, or rotate relative to the first disk; the first liquid adding mechanism and the second liquid adding mechanism are mounted on the second disk, and are configured for liquid addition to the digestion vessel.

In some embodiments, the driving mechanism comprises a lifter and a rotating motor; the lifter is connected to the rotating motor; one of the lifter and the rotating motor is connected to the base, and the other of the lifter and the rotating motor is connected to the second disk; the lifter is configured to drive the second disk to ascend and descend; and the rotating motor is configured to drive the second disk to rotate.

By virtue of the above arrangement, lift and rotation functions of the second disk relative to the first disk are respectively realized by the lifter and the rotating motor, leading to independent, simple, flexible and convenient manipulation.

In some embodiments, the lifter comprises a telescopic cylinder and a mounting column; a cylinder body of the telescopic cylinder is fixedly connected to the base; the telescopic cylinder is slidably provided with a piston rod; the piston rod is fixedly connected to the mounting column; and the rotating motor is mounted to the piston rod.

By virtue of the above arrangement, the lifter is mounted on the base, and the rotating motor is mounted to the mounting column. In this way, the rotating motor only needs to drive the second disk to rotate, and does not need to drive the lifter to rotate together, such that during operation, the load driven by the rotating motor is small, less shaking during rotation, which results in a low degree of shaking and a higher rotation stability.

In some embodiments, the second disk is rotatably fitted with the mounting column via a bearing; a first transmission gear is mounted on the second disk; a second transmission gear is mounted to an output shaft of the rotating motor; and the first transmission gear is engaged with the second transmission gear.

By virtue of the above arrangement, the second disk is connected to the mounting column through the bearing. Therefore, the second disk is guided and positioned by virtue of the mounting column, leading to a more solid positioning of the second disk. The second disk is not directly mounted on the output shaft of the rotating motor, so a centrifugal force generated when the second disk rotates does not directly act on the output shaft of the rotating motor. As a result, the rotating motor mainly serves for torque transmission, leading to a long service life of the rotating motor. The torque of the rotating motor is transmitted to the second disk by virtue of the cooperation of the first transmission gear and the second transmission gear, so that the second disk is driven to rotate around the mounting column. As being supported by the mounting column, the second disk undergoes less shaking during rotation, which results in a smoother rotation, thereby facilitating precise control of a rotation angle of the second disk relative to the first disk.

In some embodiments, each of the first liquid adding mechanism and the second liquid adding mechanism comprises a container, a quantitative liquid dispenser and an electric cylinder; the container is mounted on the second disk; the quantitative liquid dispenser is mounted on the container; an inlet of the quantitative liquid dispenser is communicated with the container, and an outlet of the quantitative liquid dispenser is configured to allow the liquid to enter the digestion vessel; and the electric cylinder is connected to the quantitative liquid dispenser, and is configured to drive the quantitative liquid dispenser to operate.

Based on the above arrangement, the quantitative addition of liquid to the quantitative liquid dispenser is realized by means of the electric cylinder, leading to a high degree of automation, high efficiency, and a more accurate amount of liquid addition.

In some embodiments, the container is provided with a liquid adding port.

Based on the above arrangement, when the amount of liquid in the container is insufficient, liquid adding port can be opened so as to add the liquid, which results in convenient operation and facilitates the continuation of the experiment.

In some embodiments, the first disk is provided with a positioning groove, and the digestion vessel is detachably inserted into the positioning groove.

Based on the above arrangement, the digestion vessel is positioned relying on the positioning groove, so that the digestion vessel is accurately and reliably located on the first disk, and is firmly positioned, which facilitates the use of the liquid adding mechanisms to add liquid to the digestion vessel.

In some embodiments, a thermal conductive sleeve is fixedly arranged in the positioning groove, and is configured to protrude outward relative to a notch of the positioning groove; the thermal conductive sleeve is provided with a stepped groove; the stepped groove comprises a first groove section and a second groove section; the first groove section is communicated with the second groove section; a groove width of the first groove section is greater than that of the second groove section; the digestion vessel is detachably inserted into the second groove section; and an outer peripheral surface of the digestion vessel and a peripheral wall of the first groove section have an avoidance space therebetween; and the heating mechanism is mounted between the thermal conductive sleeve and the second disk.

Based on the above arrangement, the first disk is set as a heat-insulating component, so that the heat is not easy to be dissipated, resulting in high heat utilization efficiency and a reduction of heating costs. The digestion vessel is inserted into the thermal conductive sleeve to form a large contact area. The thermal conductive sleeve is adapted to wrap the digestion vessel, such that the heat generated by the heating mechanism is transferred to the digestion vessel through the thermal conductive sleeve, which makes the digestion vessel more uniformly heated and achieves better heating effect. Moreover, the digestion vessel and the thermal conductive sleeve have an avoidance space therebetween, facilitating the taking and placing of the digestion vessel through the avoidance space to make the operation convenient.

In some embodiments, the second disk is provided with a sealing groove; a sealing plug is provided in the sealing groove; and a peripheral wall of the sealing groove and an outer peripheral surface of the sealing plug have an annular space therebetween, such that when the second disk is driven to move close to the first disk, the sealing plug is inserted into the digestion vessel to seal a mouth of the digestion vessel, and the thermal conductive sleeve and the digestion vessel are inserted into the annular space.

Based on the above arrangement, the thermal conductive sleeve is inserted into the sealing groove, such that a notch of the second groove section of the thermal conductive sleeve is sealed. In this way, the heat transferred from the thermal conductive sleeve to the digestion vessel is not easily dispersed from a notch of the thermal conductive sleeve, resulting in high heat utilization efficiency. Moreover, by virtue of the contact between the thermal conductive sleeve and a bottom groove wall of the sealing groove, an insertion depth of the sealing plug into the digestion vessel can be limited to improve the accuracy of the insertion position of the sealing plug, making it less likely to be inserted too deep or not deep enough.

In some embodiments, the soil sample digestion device further comprises a humidity sensor; wherein the humidity sensor is mounted to the second disk, and is configured to be inserted into the digestion vessel to acquire a humidity in the digestion vessel.

Based on the above arrangement, the humidity sensor is adapted to acquire the humidity in the digestion vessel to facilitate the control of a heating state, i.e., during heating, as the solution is evaporated, the humidity in the digestion vessel gradually decreases, and when the humidity in the digestion vessel decreases to a certain value, the heating is stopped.

Compared to the prior art, the present disclosure has the following beneficial effects.

For the soil sample digestion device of the present disclosure, during the experiment, a preset amount of a soil sample is placed in the digestion vessel, and different liquids are stored in the two liquid adding mechanisms, respectively, such as nitric acid and hydrofluoric acid. Then, the second disk is driven by the driving mechanism to move, so that the two liquid adding mechanisms are sequentially driven to move to a position where the digestion vessel is located to add corresponding amounts of the two liquids into the digestion vessel. At an initial stage, the heating mechanism is activated to heat and evaporate the solution in the digestion vessel when a mouth of the digestion vessel is open. Then, the liquid is proceeded to be added, and the second disk is driven to move close to the first disk, so that the mouth of the digestion vessel on the first disk is sealed by the second disk. The digestion vessel is heated by the heating mechanism again. After the heating is completed, the digestion vessel is taken out, and the soil sample in the digestion vessel is detected and analyzed.

During the entire experiment process, the relative position of the two liquid adding mechanisms with respect to the digestion vessel is automatically adjusted by the driving mechanism, and the two liquid adding mechanisms can realize automatic liquid addition. The whole process is highly automated with close cooperation among all of the components, resulting in low labor intensity, high test efficiency and high accuracy of test results due to less manual involvement, and less likely to cause damage the health of an operator.

BRIEF DESCRIPTION OF THE DRAWINGS

In order to illustrate the technical solutions in the embodiments of the present disclosure more clearly, the drawings needed in the description of embodiments will be briefly introduced below. It should be understood that presented in the drawings are only some embodiments of the present disclosure, which are not intended to limit the disclosure. For those of ordinary skill in the art, other related drawings can be obtained based on these drawings without exerting creative efforts.

In the drawings: 100—base; 101—mounting cavity; 200—driving mechanism; 210—lifter; 211—telescopic cylinder; 212—mounting column; 213—bearing; 220—rotating motor; 230—first transmission gear; 240—second transmission gear; 300—first disk; 310—positioning groove; 320—thermal conductive sleeve; 321—avoidance space; 400—heating mechanism; 500—digestion vessel; 600—second disk; 610—sealing groove; 620—sealing plug; 700—first liquid adding mechanism; 710—container; 720—liquid adding unit; 721—quantitative liquid dispenser; 722—electric cylinder; 800—second liquid adding mechanism; and 900—humidity sensor.

DETAILED DESCRIPTION OF EMBODIMENTS

In order to make the purpose, technical solutions and advantages of the embodiments of the present disclosure more clearly, the technical solutions in the embodiments of the present disclosure will be clearly and completely described below in conjunction with the accompanying drawings of the present disclosure. Obviously, described herein are merely some embodiments of the present disclosure, rather than all embodiments. Generally, components of the embodiments of the present disclosure described herein and shown in the drawings can be arranged and designed in various configurations.

Therefore, the following detailed description of the embodiments of the present disclosure provided in the accompanying drawings is not intended to limit the scope of the disclosure, and are merely illustrative. Based on the embodiments of the present disclosure, all other embodiments obtained by those of ordinary skill in the art without making creative efforts shall fall within the scope of the present disclosure.

It should be noted that similar reference numerals and letters denote similar items in the drawings. Therefore, once an item is defined in one drawing, further definition and explanation thereof is not required in subsequent drawings.

In the description of the embodiments, it should be noted that orientation or positional relationships related to orientation descriptions, such as "center", "up", "down", "left", "right", "vertical", "horizontal", "inside" and "outside", are based on orientation or position relationships shown in the drawings or the conventional placement of the product when it is used, which are merely intended to facilitate the description of the embodiments and simplify the description, and are not intended to indicate or imply that a device or element referred to must have a specific orientation, be constructed and operated in a specific orientation. Therefore, these orientation or positional relationships cannot be construed as limiting the present disclosure. In addition, terms "first", "second", "third", etc. are only descriptive, and cannot be understood as indicating or implying relative importance.

Moreover, terms "horizontal", "vertical", etc. do not indicate that the components are required to be absolutely horizontal or vertical, and can be slightly tilted. For example, the term "horizontal" merely means that the indicated direction is more horizontal than "vertical", and does not mean that the structure must be completely horizontal, but can be slightly inclined instead.

In the description of the embodiments, it is also necessary to explain that, unless otherwise clearly specified and limited, terms such as "arrange", "mount", "connect" and "communicate" should be understood in a broad sense. For example, it can be a fixed connection, a detachable connection, or an integrated connection; it can be a mechanical connection or an electrical connection; it can be a direct connection or an indirect connection through an intermediate medium, it can be an internal connection of two elements or an interaction relationship between two elements. For those of ordinary skill in the art, the specific meanings of the above terms in the present disclosure can be understood according to specific circumstances.

In the prior art, during the soil sample digestion test, the operations are basically carried out manually, such as adding liquid to the sample, placing the sample on a heating element for heating, and then adding liquid. This results in high labor intensity and low efficiency. Moreover, more manual involvement may lead to large errors, resulting in lower accuracy of test results.

In view of this, this application provides a soil sample digestion device with high automation, high efficiency, less manual involvement and high accuracy of test results.

Figure 1:
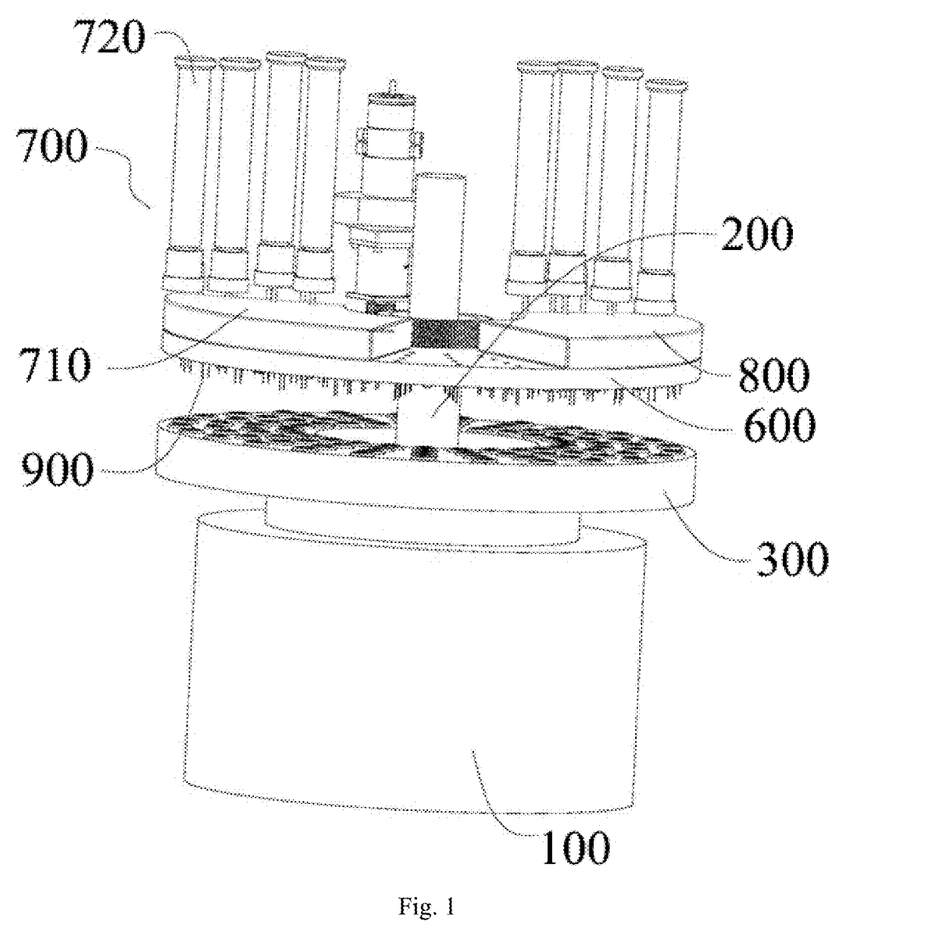
FIG. 1 is a schematic diagram of a soil sample digestion device in accordance with an embodiment of the present disclosure.
Figure 2:
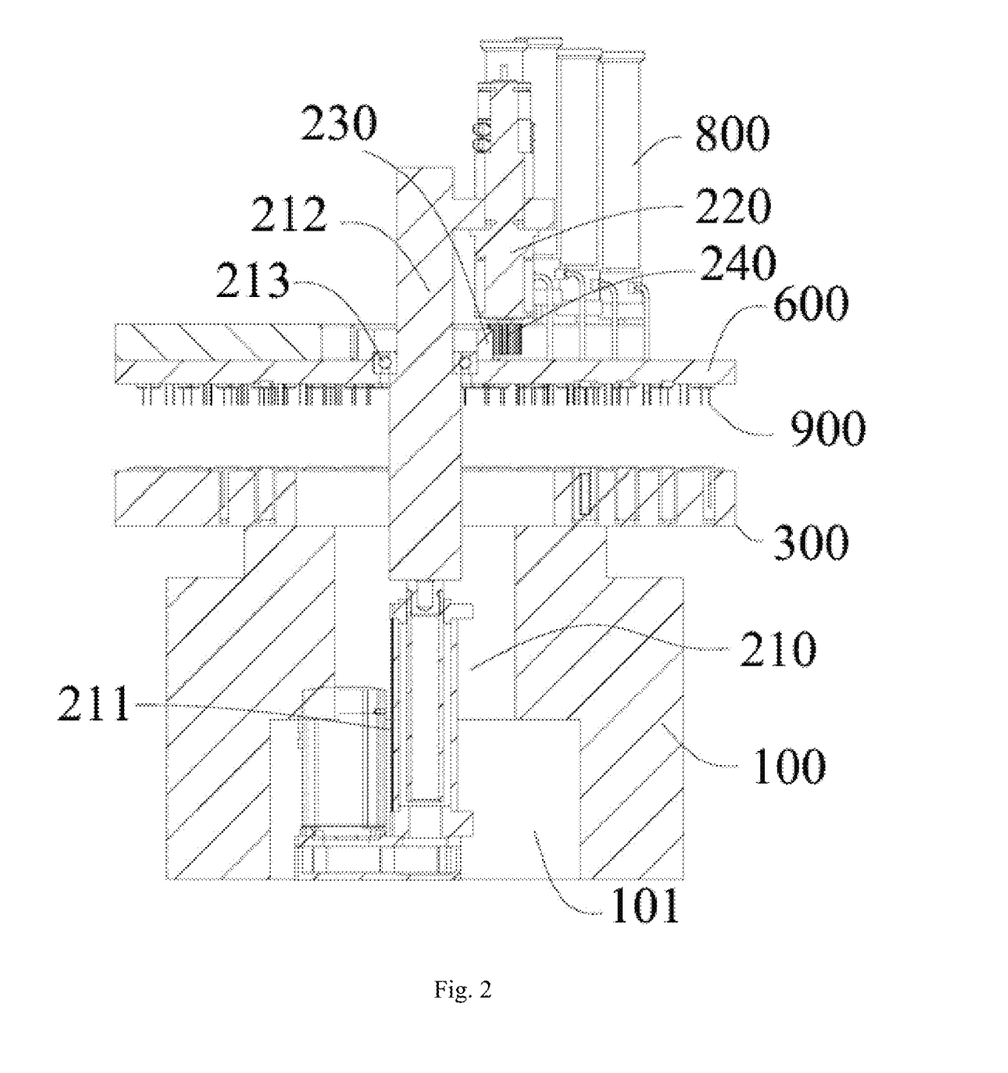
FIG. 2 is a cross-sectional view of the soil sample digestion device in accordance with an embodiment of the present disclosure.

Referring to FIGS. 1-2, provided herein is a soil sample digestion device, including a base 100, a driving mechanism 200, a first disk 300, a heating mechanism 400, a digestion vessel 500, a second disk 600 and two liquid adding mechanisms. The driving mechanism 200 and the first disk 300 are mounted on the base 100. The heating mechanism 400 and the digestion vessel 500 are mounted on the first disk 300. The heating mechanism 400 is configured to heat a solution in the digestion vessel 500. The second disk 600 is mounted on the driving mechanism 200, and is configured to be driven by the driving mechanism 200 to ascend and descend, or rotate relative to the first disk 300. The two liquid adding mechanisms are mounted on the second disk 600, and are configured for liquid addition to the digestion vessel, respectively.

In view of the foregoing, the soil sample digestion device has the following operating principle.

During the experiment, a preset amount of a soil sample is placed in the digestion vessel 500. Different liquids are stored in the two liquid adding mechanisms, respectively. In an embodiment, a nitric acid and a hydrofluoric acid are stored in the two liquid adding mechanisms, respectively. Then, the second disk 600 is driven by the driving mechanism 200 to move, so that the two liquid adding mechanisms are sequentially driven to move to a position where the digestion vessel 500 is located to add corresponding amounts of the two liquids into the digestion vessel 500. At an initial stage, the heating mechanism 400 is activated to heat and evaporate the solution in the digestion vessel 500 when a mouth of the digestion vessel 500 is open. Then, the liquid is proceeded to be added, and the second disk 600 is driven to move close to the first disk 300, so that the mouth of the digestion vessel 500 on the first disk 300 is sealed by the second disk 600. The digestion vessel 500 is heated by the heating mechanism 400 again. After the heating is completed, the digestion vessel 500 is taken out, and the soil sample in the digestion vessel 500 is detected and analyzed. During the entire experiment process, the relative position of the two liquid adding mechanisms with respect to the digestion vessel 500 is automatically adjusted by the driving mechanism 200, and the two liquid adding mechanisms can realize automatic liquid addition. The whole process is highly automated with close cooperation among all of the components, resulting in low labor intensity, high test efficiency and high accuracy of test results due to less manual involvement.

The structure of the soil sample digestion device of the present disclosure will be described in detail below.

Referring to FIGS. 1-2, in this embodiment, the soil sample digestion device includes the base 100, the driving mechanism 200, the first disk 300, the heating mechanism 400, the digestion vessel 500, the second disk 600, a first liquid adding mechanism 700, a second liquid adding mechanism 800 and a humidity sensor 900.

In an embodiment, the base 100 serves to support the entire device, and can be placed on a workbench. In this embodiment, the base 100 has a cylindrical structure, and is provided with a circular hole at the center, which is configured as a mounting cavity 101 for some components.

Referring to FIG. 2, in an embodiment, the driving mechanism 200 includes a lifter 210, a rotating motor 220, a first transmission gear 230 and a second transmission gear 240. The lifter 210 includes a telescopic cylinder 211, a mounting column 212 and a bearing 213. The telescopic cylinder 211 can be an air cylinder, a hydraulic cylinder, etc. The telescopic cylinder 211 is arranged in the mounting cavity 101. A cylinder body of the telescopic cylinder 211 is fixed to a bottom of the base 100. A piston rod is inserted in the cylinder body, and is allowed to slide reciprocally in a vertical direction relative to the cylinder body to achieve lifting and lowering. The mounting column 212 has a cylindrical structure. An end portion of the mounting column 212 is fixed to an end portion of the piston rod. An inner ring of the bearing 213 is sleevedly arranged outside the mounting column 212. The rotating motor 220 is fixed to the mounting column 212 and is located above the bearing 213. An output shaft of the rotating motor 220 is parallel to the mounting column 212. The second transmission gear 240 is sleevedly fixed to the output shaft of the rotating motor 220. The first transmission gear 230 is mounted on the second disk 600, and is engaged with the second transmission gear 240. A transmission ratio of the second transmission gear 240 to the first transmission gear 230 is greater than 1, i.e., a torque output is transmitted from the rotating motor 220 to the first transmission gear 230 through the second transmission gear 240 to realize deceleration transmission.

In a practical operation process, the telescopic cylinder 211, after being activated, enables to drive the mounting column 212, the rotating motor 220 and the second disk 600 to ascend and descend together. After the rotating motor 220 is activated, since the rotating motor 220 is fixed to the mounting column 212, and the mounting column 212 is fixed to the base 100 through the telescopic cylinder 211, i.e., the mounting column 212 would not rotate relative to the base 100, the torque can be transmitted to the second disk 600 by virtue of the cooperation of the first transmission gear 230 and the second transmission gear 240, thereby driving the second disk 600 to rotate. Since the second disk is connected to the mounting column 212 through the bearing 213, the second disk 600 is guided and positioned by virtue of the mounting column 212, leading to a more solid positioning of the second disk 600. The second disk is not directly mounted to the output shaft of the rotating motor 220, so a centrifugal force generated when the second disk 600 rotates does not directly act on the output shaft of the rotating motor 220. As a result, the rotating motor 220 mainly serves for torque transmission, leading to a long service life of the rotating motor 220. The torque of the rotating motor 220 is transmitted to the second disk 600 by virtue of the cooperation of the first transmission gear 230 and the second transmission gear 240, so that the second disk 600 is driven to rotate around the mounting column 212. As being supported by the mounting column 212, the second disk 600 undergoes less shaking during rotation, which results in a smoother rotation, thereby facilitating precise control of a rotation angle of the second disk 600 relative to the first disk 300.

Figure 3:
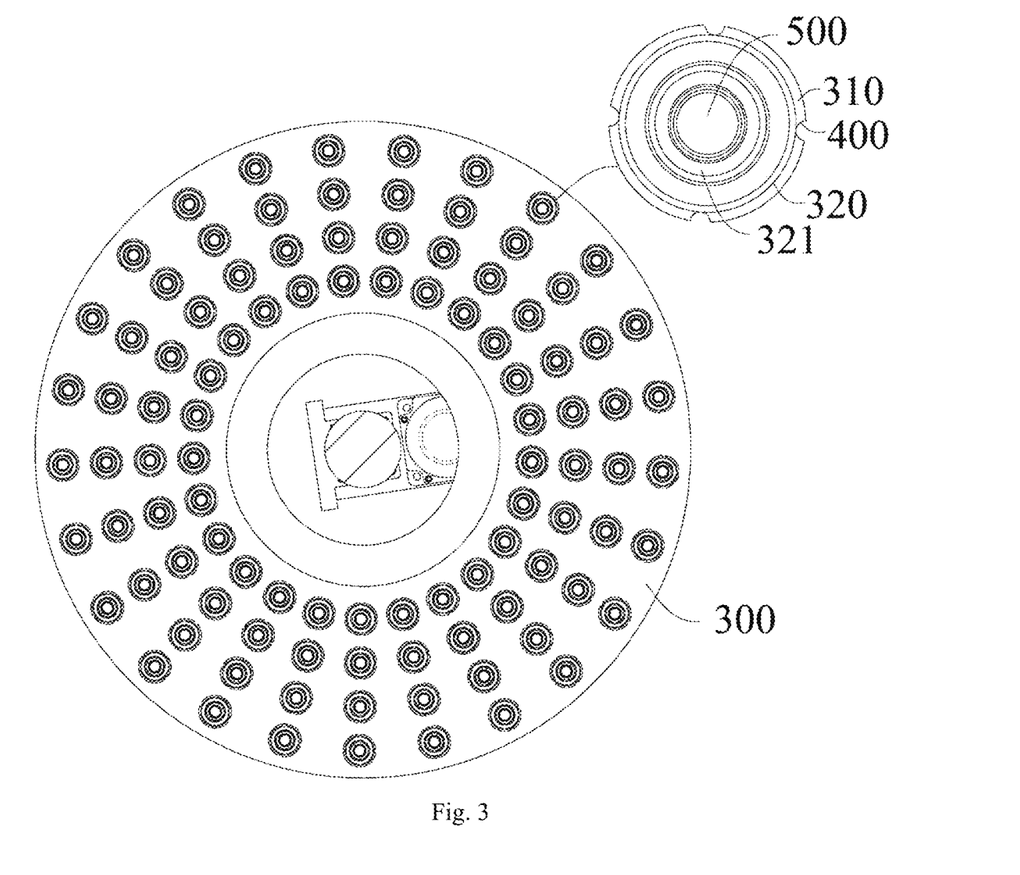
FIG. 3 is a schematic diagram of a first disk in accordance with an embodiment of the present disclosure.

Referring to FIG. 3, in this embodiment, the first disk 300 is a disk with a hollow structure, and is made of a heat-insulating material, that is, the first disk 300 can be a heat-insulating component, so that the heat is not easy to be dissipated. The mounting column 212 passes through the first disk 300, and is coaxially arranged with the first disk 300, with no interference therebetween. A plurality of positioning units are arranged on the first disk 300. Each of the plurality of positioning units includes a plurality of positioning grooves 310 that are arranged at intervals in a radial direction of the first disk 300. In this embodiment, each of the plurality of positioning units includes four positioning grooves 310 that are arranged at intervals in the radial direction of the first disk 300. The four positioning grooves 310 are cylindrical grooves. The plurality of positioning units are arranged at intervals in a circumferential direction of the first disk 300. The number of the plurality of positioning units is set as required, and will not be specifically limited herein. A thermal conductive sleeve 320 is fixedly inserted in each positioning groove 310. The thermal conductive sleeve 320 is a metal sleeve, such as a steel sleeve. The thermal conductive sleeve 320 and the positioning groove 310 have an annular space therebetween. A heating mechanism 400 is mounted in the annular space. The heating mechanism 400 can be a heating wire that is arranged between the thermal conductive sleeve 320 and a bottom wall of the positioning groove 310 and between an outer peripheral surface of the thermal conductive sleeve 320 and a peripheral wall of the positioning groove 310, so as to improve the heating efficiency. Each thermal conductive sleeve 320 is provided with a stepped groove, which includes a first groove section and a second groove section. The first groove section is communicated with the second groove section. The first groove section and the second groove section are both circular groove sections, that is, cross-sections of the first groove section and the second groove section are in a circular shape, and are perpendicular to an axis of the thermal conductive sleeve 320. The first groove section is coaxially arranged with the second groove section. A groove width of the first groove section is greater than that of the second groove section, that is, a diameter of the first groove section is greater than that of the second groove section. When in use, the digestion vessel 500 is detachably inserted into the second groove section. An outer peripheral surface of the digestion vessel 500 and a peripheral wall of the first groove section has an avoidance space 321 therebetween for an operator to place his finger therein, thereby facilitating taking and placing of the digestion vessel 500.

It should be understood that in other embodiments, the digestion vessel 500 can be set as a stepped structure, and the positioning groove 310 is a cylindrical groove. In this way, an end of the digestion vessel 500 with a larger diameter is inserted into the positioning groove 310, and an annular space can be formed between an end of the digestion vessel 500 with a smaller diameter and a groove wall of the positioning groove 310, which also facilitates taking and placing of the digestion vessel 500.

Figure 4:
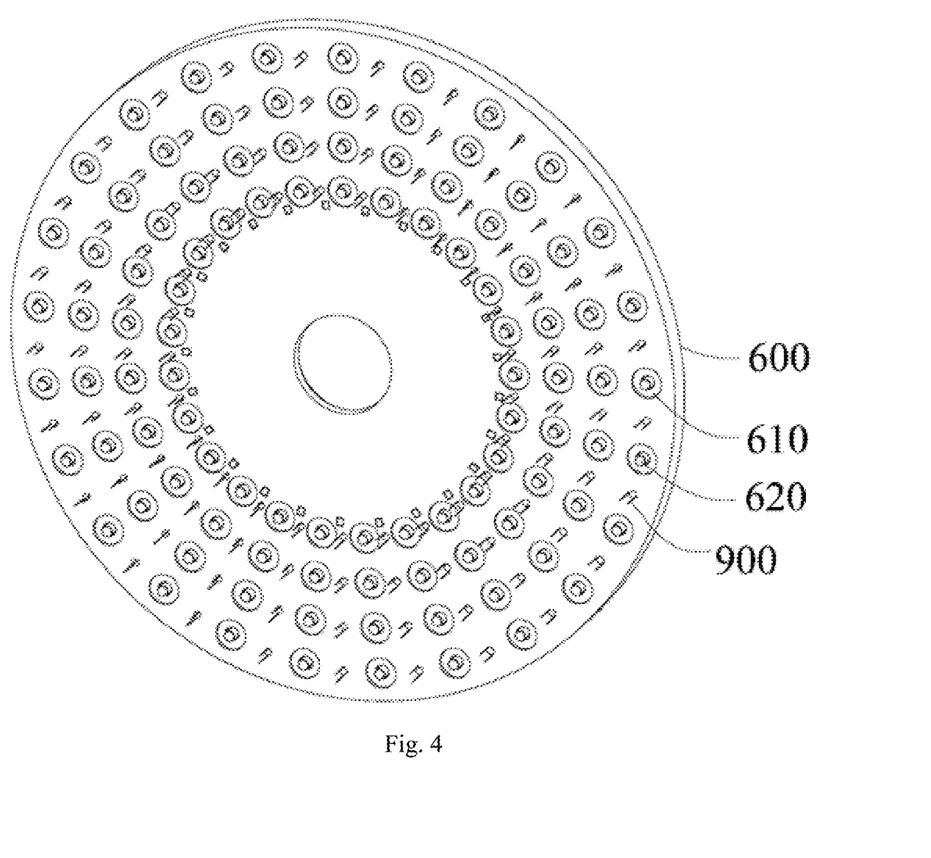
FIG. 4 is a schematic diagram of a second disk in accordance with an embodiment of the present disclosure.

Referring to FIG. 4, in this embodiment, the second disk 600 is a circular disk. The second disk 600 is sleevedly fixed to an outer ring of the bearing 213, and is coaxially arranged with the first disk 300. A plurality of sealing grooves 610 are arranged on a surface of the second disk 600 opposite to the first disk 300. The number and position of the plurality of sealing grooves 610 are in correspondence with the number and position of the thermal conductive sleeves 320. A sealing plug 620 is provided at a middle of each of the plurality of sealing groove 610. The sealing plug 620 and the sealing groove 610 have an annular space therebetween. When the second disk 600 is driven to move close to the first disk 300, the sealing plug 620 can be inserted into a corresponding digestion vessel 500 to seal the mouth of the digestion vessel 500. At the same time, an end portion of the thermal conductive sleeve 320 can be inserted into the sealing groove 610, so that a port of the thermal conductive sleeve 320 is sealed through the sealing groove 610 to reduce heat loss. Obviously, the digestion vessel 500 is partially inserted into the sealing groove 610 to avoid interference therebetween. In addition, the end portion of the thermal conductive sleeve 320 abuts against the sealing groove 610, so that a depth of the sealing plug 620 inserted into the digestion vessel 500 is limited by the contact between the thermal conductive sleeve 320 and the sealing groove 610, resulting in an accurate insertion position of the sealing plug 620 and the digestion vessel 500, thereby improving the sealing effect.

It should be noted that in this embodiment, the first liquid adding mechanism 700 and the second liquid adding mechanism 800 can be configured to have the same structure to reduce processing costs. In this embodiment, in order to avoid repeated description, only the specific structure of the first liquid adding mechanism 700 is described in detail.

Figure 5:
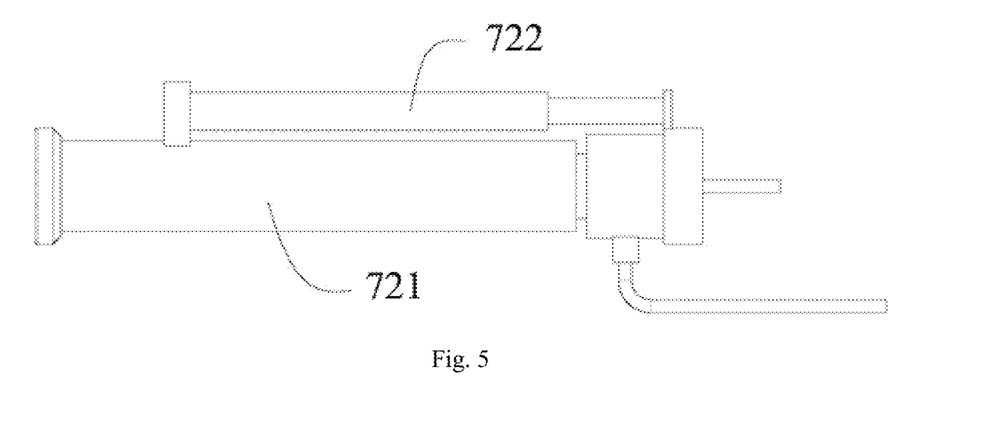
FIG. 5 is a schematic diagram of a liquid adding unit in accordance with an embodiment of the present disclosure.

Referring to FIGS. 1, 2 and 5, in an embodiment, the first liquid adding mechanism 700 includes a container 710 and four liquid adding units 720. The container 710 is fixed on the second disk 600. The four liquid adding units 720 are all connected to the container 710. The four liquid adding units 720 are in on-to-one correspondence with four digestion vessels 500 in the same positioning unit, and are each independently controlled to automatically add the liquid stored in the container 710 to the corresponding digestion vessel 500. In this way, when the second disk 600 is driven to rotate relative to the first disk 300, the four liquid adding units 720 can sequentially add liquids to the four digestion vessels 500 in each positioning units, which leads to convenient operation, high level of automation and high efficiency. For example, in a case where an angle between two adjacent positioning units is α, the second disk 600 can be manually or automatically zeroed so that the four liquid adding units 720 are aligned with one of the positioning units. Then, every time the second disc body 600 is rotated by an angle of α, the subsequent four digestion vessels 500 is subjected to liquid addition.

In an embodiment, each liquid adding unit 720 can include a quantitative liquid dispenser 721 and an electric cylinder 722. The quantitative liquid dispenser 721 is mounted on the container 710. An inlet of the quantitative liquid dispenser 721 is connected to the container 710. An outlet of the quantitative liquid dispenser 721 is configured to allow the liquid to enter the digestion vessel 500. The electric cylinder 722 is connected to the quantitative liquid dispenser 721, and is configured to drive the quantitative liquid dispenser 721 to operate. The quantitative liquid dispenser 721 can be a syringe. The syringe is provided with an inlet and an outlet on its barrel wall. A piston of the syringe is inserted into a barrel cavity of the syringe. A one-way valve is provided at the inlet of the syringe, so that only an external solution is allowed to pass through the one-way valve to enter the barrel cavity of the syringe. The electric cylinder 722 has a telescopic structure. The electric cylinder 722 is mounted to the syringe. A telescopic end of the electric cylinder 722 is connected to the piston of the syringe. The electric cylinder 722 in an extended state can drive the piston of the syringe to move, so that a volume of the barrel cavity of the syringe is increased, allowing the liquid to be sucked from the container 710 into the barrel cavity of the syringe through the inlet of the syringe. The electric cylinder 722 in a contracted state can drive the piston of the syringe to move, so that the volume of the barrel cavity of the syringe is reduced, allowing the liquid to be pressed out from the outlet of the syringe to enter the corresponding digestion vessel 500. An amount of the liquid is controlled by setting the extension and retraction distance of the electric cylinder 722, thereby realizing automatic quantitative liquid addition.

It should be understood that the liquid adding unit 720 can also have other structures that can realize automatic liquid addition.

Furthermore, the container 710 can be provided with a liquid adding port. When the amount of the liquid is insufficient, the liquid can be added manually or automatically through the liquid adding port.

In this embodiment, the number of humidity sensors 900 is consistent with the number of digestion vessels 500. A plurality of humidity sensors 900 are all mounted on the second disk 600. The humidity sensor 900 and the sealing plug 620 have a gap therebetween in a circumferential direction of the second disk 600. When the second disk 600 is driven to move close to the first disk 300, each of the plurality of humidity sensors 900 can be inserted into the corresponding digestion vessel 500, so that a humidity in the corresponding digestion vessel 500 can be acquired by the humidity sensor 900, so as to determine the heating effect. Moreover, when it is necessary to seal the digestion vessel 500 using the sealing plug 620, the second disk 600 is first lifted such that the humidity sensor 900 is separated from the digestion vessel 500. Then, the second disk 600 is rotated so that the sealing plug 620 is aligned with the digestion vessel 500.

An application example of the soil sample digestion device in this embodiment is provide below.

Step (1) 50 mg of a soil sample is manually weighed and added to the digestion vessel 500. 1.50 mL of high-purity nitric acid ($HNO_3$) is added to the digestion vessel 500 by using the first liquid adding mechanism 700. 1.50 mL of high-purity hydrofluoric acid (HF) is added to the digestion vessel 500 by using the second liquid adding mechanism 800. At this time, the digestion vessel 500 is in an open state. The digestion vessel 500 is heated by adjusting the temperature to 140° C. using the heating mechanism 400. When the humidity sensor 900 detects that the moisture inside the digestion vessel 500 is almost completely evaporated, the heating mechanism 400 is turned off to stop heating. In this step, the purpose of adding HF is to destroy silicon lattices of soil particles, so as to achieve more thorough soil digestion. However, since HF has a strong corrosive effect on utensils, the heating must be carried out in the open state to drive out the acid. Specifically, in this step, when the heating is performed, it is only necessary to drive the second disk 600 to descend close to the first disk 300 so that the humidity sensor 900 is inserted into the digestion vessel 500, with no need to seal the mouth of the digestion vessel 500.

Step (2) 3 mL of high-purity HNO₃ is added to the digestion vessel 500. The second disk 600 is driven by the driving mechanism 200 to descend, such that the sealing plug 620 is inserted into the digestion vessel 500 to seal the mouth of the digestion vessel 500. The digestion vessel 500 in a sealed state is kept at 195° C. for more than 48 h. Then, the second disk 600 is driven by the driving mechanism 200 to ascend, such that the sealing plug 620 is separated from the digestion vessel 500. The heating mechanism 400 is started. When the humidity sensor 900 detects that the moisture inside the digestion vessel 500 is almost completely evaporated, the heating mechanism 400 is turned off to stop heating.

Step (3) 3 mL of HNO₃ is added to the digestion vessel 500. The second disk 600 is driven to descend, such that the mouth of the digestion vessel 500 is sealed by the sealing plug 620. The digestion vessel 500 is dried in an oven at 150° C. for 24 h to ensure that the soil sample is completely extracted. After the soil sample is cooled, the second disk 600 is driven to ascend, such that the sealing plug 620 is separated from the digestion vessel 500. The digestion vessel 500 is taken out from the first disk 300.

For the soil sample digestion device provided in this embodiment, the second disk 600 is driven by the driving mechanism 200 to rotate, ascend and descend relative to the first disk 300, such that the relative position of the sealing plug 620 relative to the digestion vessel 500 is adjusted as required. Moreover, by virtue of the cooperation of the liquid adding mechanisms and the driving mechanism 200, the automatic addition of liquid into the digestion vessel 500 is achieved. The whole process has a high degree of automation, high efficiency, less manual intervention, and high accuracy of the test results.

The embodiments described above are merely illustrative of the present application, and are not intended to limit the scope of the present application. Any modifications, equivalent replacements and improvements made by those skilled in the art without departing from the spirit of the disclosure shall fall within the scope of the disclosure defined by the appended claims.

What is claimed is:

1. A soil sample digestion device, comprising:
   a base;
   a driving mechanism;
   a first disk;
   a heating mechanism;
   a digestion vessel;
   a second disk;
   a first liquid adding mechanism;
   a second liquid adding mechanism; and
   a humidity sensor;
   wherein the driving mechanism and the first disk are mounted on the base; the heating mechanism and the digestion vessel are mounted on the first disk; the heating mechanism is configured to heat a solution in the digestion vessel; the second disk is mounted on the driving mechanism, and is configured to be driven by the driving mechanism to ascend and descend, or rotate relative to the first disk; and the first liquid adding mechanism and the second liquid adding mechanism are mounted on the second disk, and are configured for liquid addition to the digestion vessel, respectively;
   the first disk is provided with a positioning groove, and the digestion vessel is detachably inserted into the positioning groove; and a thermal conductive sleeve is fixedly arranged in the positioning groove, and is configured to protrude outward relative to a notch of the positioning groove;
   the second disk is provided with a sealing groove; a sealing plug is provided in the sealing groove; and a peripheral wall of the sealing groove and an outer peripheral surface of the sealing plug have an annular space therebetween, such that when the second disk is driven to move close to the first disk, the sealing plug is inserted into the digestion vessel to seal a mouth of the digestion vessel, and the thermal conductive sleeve and the digestion vessel are inserted into the annular space;
   the humidity sensor is mounted to the second disk, and is configured to be inserted into the digestion vessel to acquire a humidity in the digestion vessel; and the humidity sensor and the sealing plug have a gap therebetween in a circumferential direction of the second disk;
   the second disk is configured to be driven by the driving mechanism to rotate, or ascend and descend relative to the first disk; a relative position of the sealing plug relative to the digestion vessel is adjusted as required; and the first liquid adding mechanism and the second liquid adding mechanism are configured to cooperate with the driving mechanism to automatically add a liquid to the digestion vessel; and
   the soil sample digestion device is adapted to perform steps of:
   adding, by the first liquid adding mechanism, hydrofluoric acid to the digestion vessel containing a soil sample; adding, by the second liquid adding mechanism, nitric acid to the digestion vessel; starting the driving mechanism to drive the second disk to descend, such that the humidity sensor is inserted into the digestion vessel, and the gap is formed between the second disk and the first disk to ensure that the mouth of the digestion vessel is in an open state; and heating, by the heating mechanism, the digestion vessel with the mouth in the open state until the humidity in the digestion vessel acquired by the humidity sensor is lower than a threshold value; and
   driving, by the driving mechanism, the second disk to ascend, such that the humidity sensor is separated from the digestion vessel; adding, by the second liquid adding mechanism, the nitric acid to the digestion vessel; driving, by the driving mechanism, the second disk to descend, such that the mouth of the digestion vessel is sealed by the sealing plug; heating, by the heating mechanism, the digestion vessel with the mouth in a sealed state; and after the heating is completed, taking out the digestion vessel, and performing detection and analysis on the soil sample in the digestion vessel.

2. The soil sample digestion device of claim 1, wherein the driving mechanism comprises a lifter and a rotating motor; the lifter is connected to the rotating motor, and is configured to drive the second disk to ascend and descend; and the rotating motor is configured to drive the second disk to rotate.

3. The soil sample digestion device of claim 2, wherein the lifter comprises a telescopic cylinder and a mounting column; a cylinder body of the telescopic cylinder is fixedly connected to the base; the telescopic cylinder is slidably provided with a piston rod; the piston rod is fixedly connected to the mounting column; and the rotating motor is mounted to the piston rod.

4. The soil sample digestion device of claim 3, wherein the second disk is rotatably fitted with the mounting column via a bearing; a first transmission gear is mounted on the second disk; a second transmission gear is mounted to an output shaft of the rotating motor; and the first transmission gear is engaged with the second transmission gear.

5. The soil sample digestion device of claim 1, wherein each of the first liquid adding mechanism and the second liquid adding mechanism comprises a container, a quantitative liquid dispenser and an electric cylinder; the container is mounted on the second disk; the quantitative liquid dispenser is mounted on the container; an inlet of the quantitative liquid dispenser is communicated with the container, and an outlet of the quantitative liquid dispenser is configured to allow the liquid to enter the digestion vessel; and the electric cylinder is connected to the quantitative liquid dispenser, and is configured to drive the quantitative liquid dispenser to operate.

6. The soil sample digestion device of claim 5, wherein the container is provided with a liquid adding port.

7. The soil sample digestion device of claim 1, wherein the thermal conductive sleeve is provided with a stepped groove; the stepped groove comprises a first groove section and a second groove section; the first groove section is communicated with the second groove section; a groove width of the first groove section is greater than that of the second groove section; the digestion vessel is detachably inserted into the second groove section; and an outer peripheral surface of the digestion vessel and a peripheral wall of the first groove section have an avoidance space therebetween; and the heating mechanism is mounted between the thermal conductive sleeve and the second disk.

* * * * *